(12) United States Patent
Pazenok et al.

(10) Patent No.: US 8,969,572 B2
(45) Date of Patent: Mar. 3, 2015

(54) PROCESS FOR PREPARING TETRAZOLE-SUBSTITUTED ANTHRANILAMIDE DERIVATIVES AND NOVEL CRYSTAL POLYMORPHS OF THESE DERIVATIVES

(75) Inventors: Sergii Pazenok, Solingen (DE); Norbert Lui, Odenthal (DE); Frank Volz, Köln (DE); Britta Olenik, Bottrop (DE); Christian Funke, Leichlingen (DE); Rüdiger Fischer, Pulheim (DE); Oliver Gaertzen, Köln (DE); Martin-Holger Hinz, Hückeswagen (DE); Arnd Neeff, Burscheid (DE)

(73) Assignee: Bayer Cropscience AG, Monheim (DE)

( * ) Notice: Subject to any disclaimer, the term of this patent is extended or adjusted under 35 U.S.C. 154(b) by 163 days.

(21) Appl. No.: 13/159,961

(22) Filed: Jun. 14, 2011

(65) Prior Publication Data

US 2012/0101133 A1  Apr. 26, 2012

Related U.S. Application Data

(60) Provisional application No. 61/354,920, filed on Jun. 15, 2010.

(30) Foreign Application Priority Data

Jun. 15, 2010 (EP) .................................... 10166059

(51) Int. Cl.
C07D 401/14 (2006.01)

(52) U.S. Cl.
CPC .................................... *C07D 401/14* (2013.01)
USPC ....................................................... 546/268.4

(58) Field of Classification Search
CPC .................................................... C07D 401/14
USPC ........................................ 546/268.4; 548/253
See application file for complete search history.

(56) References Cited

U.S. PATENT DOCUMENTS

| 8,324,390 B2 * | 12/2012 | Fischer et al. ............. 546/275.4 |
| 2010/0029478 A1 | 2/2010 | Alig et al. |
| 2010/0256195 A1 | 10/2010 | Fischer et al. |

FOREIGN PATENT DOCUMENTS

| WO | 2004/020445 | 3/2004 |
| WO | 2006/023783 | 3/2006 |
| WO | 2007/144100 | 12/2007 |
| WO | 2010/069502 | 6/2010 |

OTHER PUBLICATIONS

Kirk-Othmer Encyclopedia of Chemical Technology, 8, pp. 95-147 (2002).*
Dorwald, Side Reactions in Organic Synthesis, 2005, Wiley: VCH Weinheim Preface, pp. 1-15 & Chapter 8, pp. 279-308.*
R.J.Spear "Positional Selectivity of the Methylation of 5-Substituted Tetrazolate Anions", Australian Journal of Chemistry, 1984;37: 2453-2468. XP000653166.
William P. Norris "5-Trifluoromethyltetrazole and Its Derivatives", Journal of Organic Chemistry, 1962;27(9): 3248-3251. XP002607646.
William G. Finnegan et al. "Synthesis and Reactions of 1-Nitroso-1-Alkyl-2-Guanyl-and-2-Carbamylhydrazines", 1965;30(2): 567-575. XP002607647.
Ronald A. Henry et al. "Mono-Alkylation of Sodium 5-Aminotetrazole in Aqueous Medium", Journal of the American Chemical Society, 1954;76(3): 923-926. XP002607648.
Caira M. R, "Crystalline Polymorphism of Organic Compounds", Topics in Current Chemistry, 1998;198: 163-208. XP001156954.
Richard W. Harper "Development of a Series of Phenyltetrazole Leukotriene D. (LTD) Receptor Antagonists" J. Med. Chemistry, 1992;37: 1191-1200. XP 002607645.
B. R. Baker et al. "An Antimalarial Alkaloid From Hydrangea. XV. Synthesis of 5-, 6-, 7-, and 8-Derivatives With Two Identical Substituents", Journal of Organic Chemistry, 1951: 149-153.
Peter Baur et al. "Polydisperse Ethoxylated Fatty Alcohol Surfactants as Accelerators of Cuticular Penetration. 1. Effects of Ethoxy Chain Length and the Size of the Penetrants", Pesticide Science, 1997;51: 131-152.
Dennis P. Curran et al. "Tris(2-Perfluorohexylethyl)Tin Azide: A New Reagent for Preparation of 5-Substituted Tetrazoles From Nitriles With Purification by Fluorous/Organic Liquid-Liquid Extraction", Tetrahedrom, 1999;55: 8997-9006.
Fred E. Sheibley "6,8-Dichlorobenzoylene Urea, and the Interaction of 5, 7-Dihalogen Isatoic Anhydrides with Ammonia,—A New Reagent for Sodium", Journal of Organic Chemistry, 1938;3: 414-423.

(Continued)

*Primary Examiner* — Patricia L Morris
(74) *Attorney, Agent, or Firm* — Miles & Stockbridge PC.

(57) ABSTRACT

The present invention relates to a process for preparing tetrazole-substituted anthranilamide derivatives of the formula (I)

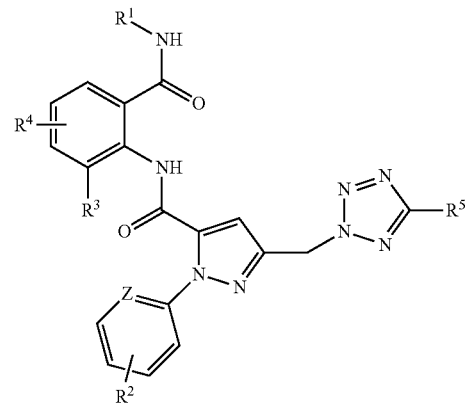

in which $R^1$, $R^2$, $R^3$, $R^4$, $R^5$ and Z are each as defined in the description, and to a novel crystal polymorph of these derivatives and to the use thereof in agrochemical formulations.

10 Claims, 7 Drawing Sheets

(56) References Cited

OTHER PUBLICATIONS

G. Reissenweber et al. "Oxidation Von Isatinen Zu Anthranilsaeureestern", Angew Chem. 1981;93: 914-915.

Henry C. Brown et al. "5-Perfluoroalkyltetrazoles. I. Ring-Opening Reactions", Journal of Organic Chemistry, 1967; 32(6): 1871-1873.

L.D. Hansen et al. "Thermodynamics of Proton Ionization from Some Substituted, Unsaturated, Five-Membered Nitrogen Heterocycles (1)"; 1970;7: 991-996.

Pedro J. Montoya-Pelaez et al. "The Synthesis and Resolution of 2,2'-, 4,4'-, and 6,6'-Substituted Chiral Biphenyl Derivatives for Application in the Preparation of Chiral Materials", Journal of Organic Chemical, 2006;71: 5921-5929.

International Search Report of PCT/EP2011/059735 Mailed Aug. 16, 2011.

* cited by examiner

PROCESS FOR PREPARING TETRAZOLE-SUBSTITUTED ANTHRANILAMIDE DERIVATIVES AND NOVEL CRYSTAL POLYMORPHS OF THESE DERIVATIVES

CROSS REFERENCE TO RELATED APPLICATIONS

This application claims priority to EP 10166059.5 filed Jun. 15, 2010 and U.S. 61/354,920 filed Jun. 15, 2010, the contents of which both are incorporated by reference in their entireties.

BACKGROUND

1. Field of the Invention

The present invention relates to a process for preparing tetrazole-substituted anthranilamide derivatives of the formula (I)

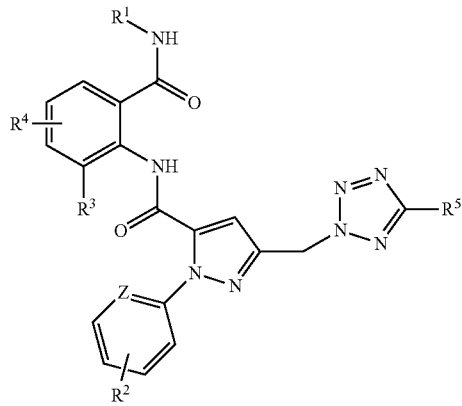

by conversion of N-aryl- and N-hetaryl-substituted pyrazoles which contain methylenetetrazole radicals. The present invention further relates to the provision of a novel crystal polymorph of the corresponding anthranilamide derivatives by this process, and to the novel crystal polymorph and to the use thereof in agrochemical formulations.

2. Description of Related Art

The literature has already stated that, for example, the alkylation of alkyltetrazoles with, for example, alkyl iodides typically leads to a mixture of different regioisomers. In addition, the composition of the mixture depends strongly on the particular substituents on the tetrazole ring. For instance, William P. Norris, in J. Org. Chem., 1962, 27 (9), 3248-3251, states that the alkylation of 5-trifluoromethyltetrazole with methyl iodide gives rise to a mixture of the two regioisomers in a ratio of 6:1. The alkylation of alkyltetrazoles leads, in contrast, usually to 1-substituted tetrazoles (see R-A. Henry et al., JACS, 76, 923 (1954).

It is likewise known that the occurrence of active ingredients in different crystal polymorphs (polymorphism) is of great significance both for the development of preparation processes and for the development of formulations. For instance, the different crystal polymorphs of a chemical compound, in addition to appearance (crystal habit) and hardness, also differ in numerous further physicochemical properties. Differences with regard to stability, filterability, solubility, hygroscopicity, melting point, solid density and flowability can exert a strong influence on the quality and efficacy of crop treatment compositions. It has not been possible to date to forecast the occurrence and number of crystal polymorphs, including the physicochemical properties thereof. In particular, the thermodynamic stability and also the different behaviour after administration to living organisms cannot be determined in advance.

SUMMARY

It is therefore an object of the present invention to provide novel, economically viable processes for preparing tetrazole-substituted anthranilamide derivatives of the formula (I) in higher purity and better quality, the intention being especially to minimize the proportion of isomers which have a bond at the 1 position of the tetrazole ring. It is a further object of the present invention to provide a novel crystal polymorph of corresponding anthranilamide derivatives which, due to its physicochemical properties, is easy to handle and enables the production of a stable formulation.

The object has been achieved in accordance with the invention by a process for preparing anthranilamide derivatives of the general formula (I)

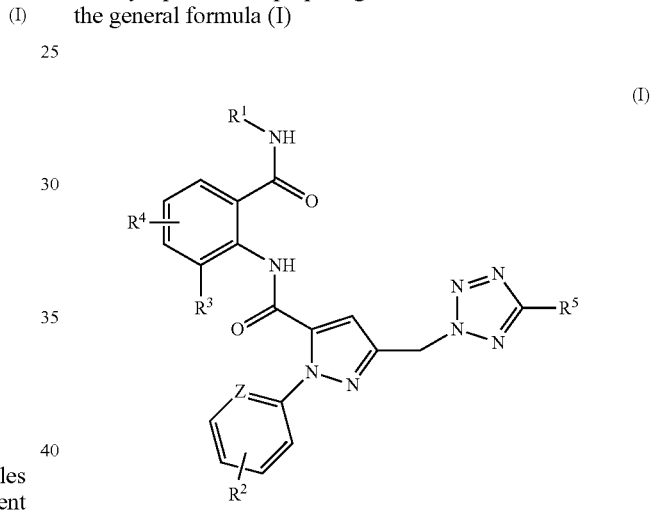

in which $R^1$, $R^3$ are each independently hydrogen, optionally singly or multiply, identically or differently halogen- or nitro-substituted $C_1$-$C_6$-alkyl, $C_1$-$C_6$-alkoxy, $C_2$-$C_6$-alkenyl, $C_2$-$C_6$-alkynyl or $C_3$-$C_6$-cycloalkyl, preferably ($C_1$-$C_5$)-alkyl, more preferably methyl, ethyl or tert-butyl, most preferably methyl, R2 is C1-C6-alkyl, C3-C6-cycloalkyl, C1-C6-haloalkyl, C1-C6-halocycloalkyl, C2-C6-alkenyl, C2-C6-haloalkenyl, C2-C6-alkynyl, C2-C6-haloalkynyl, C1-C4-alkoxy, C1-C4-haloalkoxy, C1-C4-alkylthio, C1-C4-alkylsulphinyl, C1-C4-alkylsulphonyl, C1-C4-haloalkylthio, C1-C4-haloalkylsulphinyl, C1-C4-haloalkylsulphonyl, halogen, cyano, nitro, alkylamino, dialkylamino, cycloalkylamino or C3-C6-trialkylsilyl, preferably halogen or C1-C6-alkyl, more preferably fluorine or chlorine, most preferably chlorine, R4 is hydrogen, halogen, cyano, nitro, C1-C4-alkyl, C1-C4-haloalkyl, C2-C6-alkenyl, C2-C6-haloalkenyl, C2-C6-alkynyl, C1-C4-alkoxy, C1-C4-haloalkoxy, SF5, C1-C4-alkylthio, C1-C4-alkylsulphinyl, C1-C4-alkylsulphonyl, C1-C4-haloalkylthio, C1-C4-haloalkylsulphinyl, C1-C4-haloalkylsulphonyl, C1-C4-alkylamino, di(C1-C4-alkyl)amino, C3-C6-cycloalkylamino, (C1-C4-alkoxy)imino, (C1-C4-alkyl)(C1-C4-alkoxy)imino, (C1-C4-haloalkyl)(C1-C4-cyano, nitro, alkoxy)imino or C3-C6-trialkylsilyl, preferably hydrogen, chlorine or cyano, more preferably chlorine or cyano, most preferably cyano, R5 is C1-C5-alkyl which may be mono- to trisubstituted by halogen, preferably C1-C3-perfluoroalkyl, more preferably $CF_3$ or $C_2F_5$, most preferably $CF_3$, Z is CH and N, preferably N, the compounds of the general formula (I) also include N-oxides and salts, characterized in that N-aryl- and N-hetaryl-substituted pyrazoles of the formula (II)

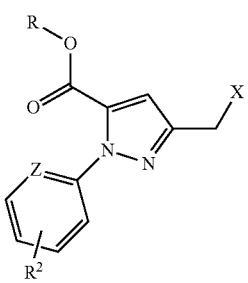

(II)

in which

R is $(C_1-C_6)$-alkyl, aryl$(C_1-C_6)$-alkyl or aryl, $R^2$, Z are each as defined above and X is fluorine, chlorine, bromine, iodine, $CH_3SO_2O$, $CF_3SO_3$, or p-$CH_3$—$C_6H_4SO_3$, are reacted with tetrazoles of the formula (III)

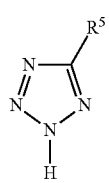

(III)

in which $R^5$ is as defined above to give pyrazolecarboxylic esters of the formula (IV)

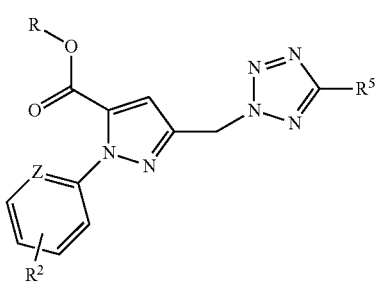

(IV)

in which

R, R2, R5 and Z are each as defined above, and the latter are optionally converted without preceding isolation to pyrazolecarboxylic acids of the formula (V)

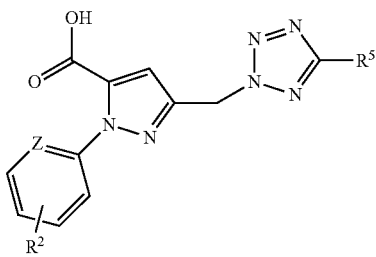

(V)

in which R2, R5 and Z are each as defined above
and the latter are reacted with compounds of the general formula (VI)

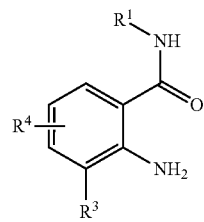

(VI)

where R1, R3, R4 are each as defined above
to give anthranilamides of the formula (I)

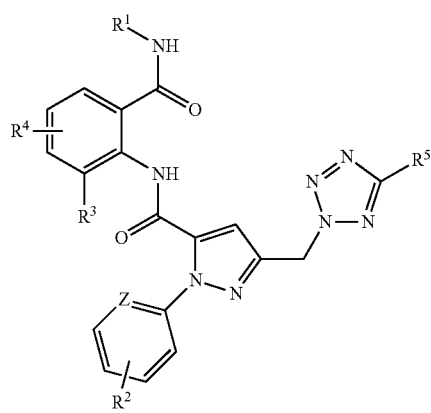

(I)

in which $R^1$, $R^2$, $R^3$, $R^4$, $R^5$ and Z are each as defined above.

BRIEF DESCRIPTION OF THE DRAWINGS

FIG. 1 describes a x-ray powder diffractogram of polymorph B.

FIG. 2 describes a comparison of polymorph A and B.

FIG. 3 describes a raman spectrum of polymorph A.

FIG. 4 describes a raman spectrum of polymorph B.

FIG. 5 describes an spectrum of polymorph A.

FIG. 6 describes an spectrum of polymorph A

FIG. 7 describes example 1 of after storage at room temperature for 3 days (left side: form A; right side: form B).

FIG. 8 describes example 1 after storage at room temperature for 3 days and at 40° C. for 7 days (left side: form A; right side: form B).

FIG. 9 describes example 1 after storage at room temperature for 3 days and at 54° C. for 7 days (left side: form A; right side: form B).

FIG. 10 describes example 1 form a after storage at 54° C. (left side: form A; right side: form B)

FIG. 11 describes example 2 after storage at room temperature for 3 days and at 40° C. for 7 days (left side: form A; right side: form B).

FIG. 12 describes example 2 after storage at room temperature for 3 days and at 54° C. for 7 days (left side: form A; right side: form B).

FIG. 13 describes example 2 Microscope Form B after storage at 54° C.; right side image: Form A after storage at 54° C.; left side.

FIG. 14 describes example 3 after storage at room temperature for 3 days and at 40° C. for 14 days (left side: form A; right side: form B).

FIG. 15 describes example 3 after storage at room temperature for 3 days and at 54° C. for 14 days (left side: form A; right side: form B).

DETAILED DESCRIPTION OF A PREFERRED EMBODIMENT

Figure 1:
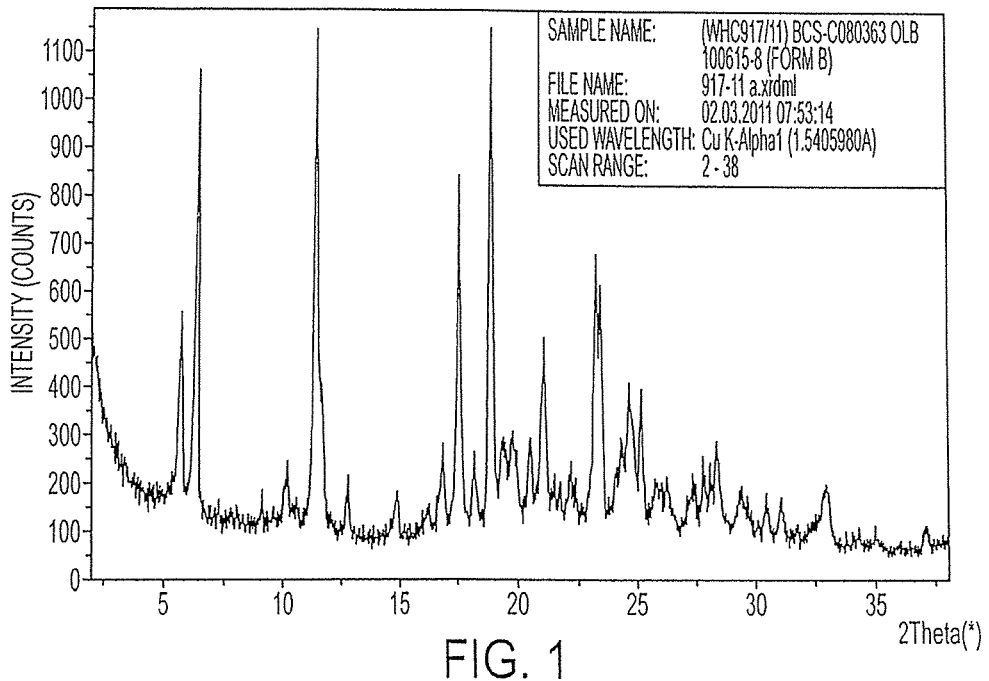
FIGS. 1-15 depict spectra according to the instant disclosure.

The inventive process affords the compounds of the formula (I) with a purity of >90%, preferably of 91%-97%, more preferably of 93% to 97%. The 1 isomer, which is bonded at the 1 position of the tetrazole ring, forms only to an extent of 5-10%.

The process according to the invention can be illustrated by the following Scheme, (I):

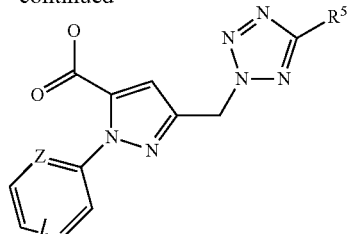

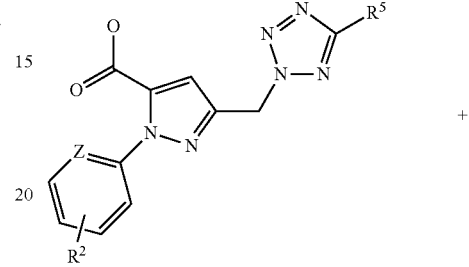

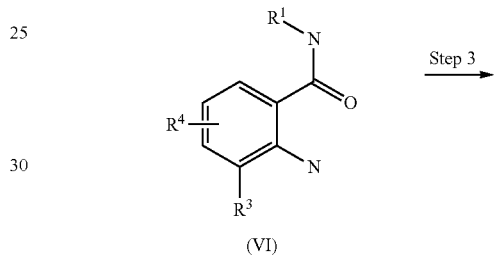

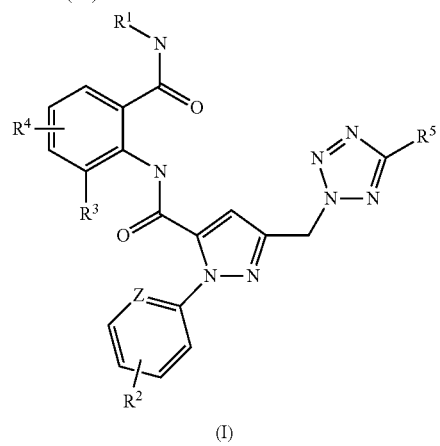

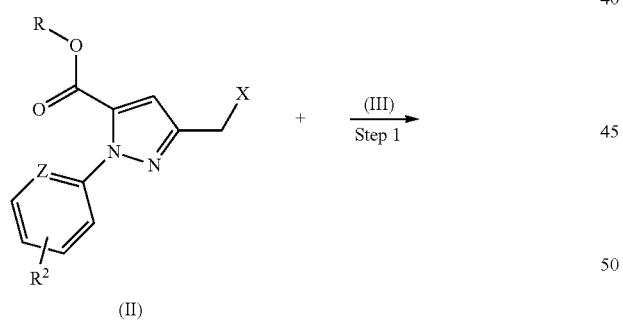

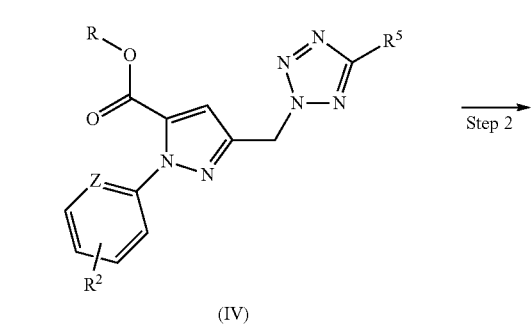

in which $R^1$, $R^2$, $R^3$, R, $R^4$, $R^5$, Z and X each have the above-specified general definitions, where $R^1$ in formula VI (step 3) is not hydrogen.

Scheme (I)

General Definitions

In the context of the present invention, the term "halogens" (X) includes, unless defined differently, those elements selected from the group consisting of fluorine, chlorine, bromine and iodine, preference being given to using fluorine, chlorine and bromine, and particular preference to using fluorine and chlorine. Substituted groups may be mono- or polysubstituted, where the substituents in the case of polysubstitutions may be the same or different.

Alkyl groups substituted by one or more halogen atoms (—X)=(haloalkyl groups) are, for example, selected from trifluoromethyl ($CF_3$), difluoromethyl ($CHF_2$), $CCl_3$, $CFCl_2$, $CF_3CH_2$, $ClCH_2$, $CF_3CCl_2$.

Alkyl groups in the context of the present invention, unless defined differently, are linear or branched hydrocarbyl groups.

The definition "alkyl" and "$C_1$-$C_{12}$-alkyl" includes, for example, the meanings of methyl, ethyl, n-, isopropyl, n-, iso-, sec- and t-butyl, n-pentyl, n-hexyl, 1,3-dimethylbutyl, 3,3-dimethylbutyl, n-heptyl, n-nonyl, n-decyl, n-undecyl, n-dodecyl.

Cycloalkyl groups in the context of the present invention, unless defined differently, are cyclic saturated hydrocarbyl groups.

Aryl radicals in the context of the present invention, unless defined differently, are aromatic hydrocarbyl radicals which may have one, two or more heteroatoms selected from O, N, P and S, and may optionally be substituted by further groups.

Arylalkyl groups and arylalkoxy groups in the context of the present invention, unless defined differently, are alkyl or alkoxy groups which are substituted by aryl groups and may have an alkylene chain. Specifically, the definition "arylalkyl" includes, for example, the meanings of benzyl and phenylethyl; the definition "arylalkoxy" includes, for example, the meaning of benzyloxy.

Alkylaryl groups (alkaryl groups) and alkylaryloxy groups in the context of the present invention, unless defined differently, are aryl groups or aryloxy groups which are substituted by alkyl groups and may have a C1-8-alkylene chain, and may have one or more heteroatoms selected from O, N, P and S in the aryl skeleton or aryloxy skeleton.

The inventive compounds may be present as mixtures of different possible isomeric forms, especially of stereoisomers, for example E and Z isomers, threo and erythro isomers, and optical isomers, but if appropriate also of tautomers. Both the E and the Z isomers are claimed, as are the threo and erythro isomers, and also the optical isomers, any mixtures of these isomers, and also the possible tautomeric forms.

More particularly, the process according to the invention provides a novel crystal polymorph of the following compound of the formula (I-1)

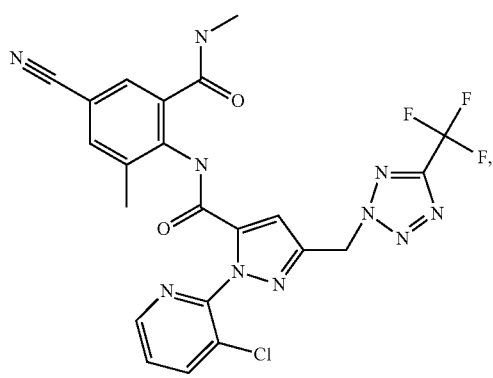

(I-1)

which is referred to below as crystal polymorph B.

Figure 2:
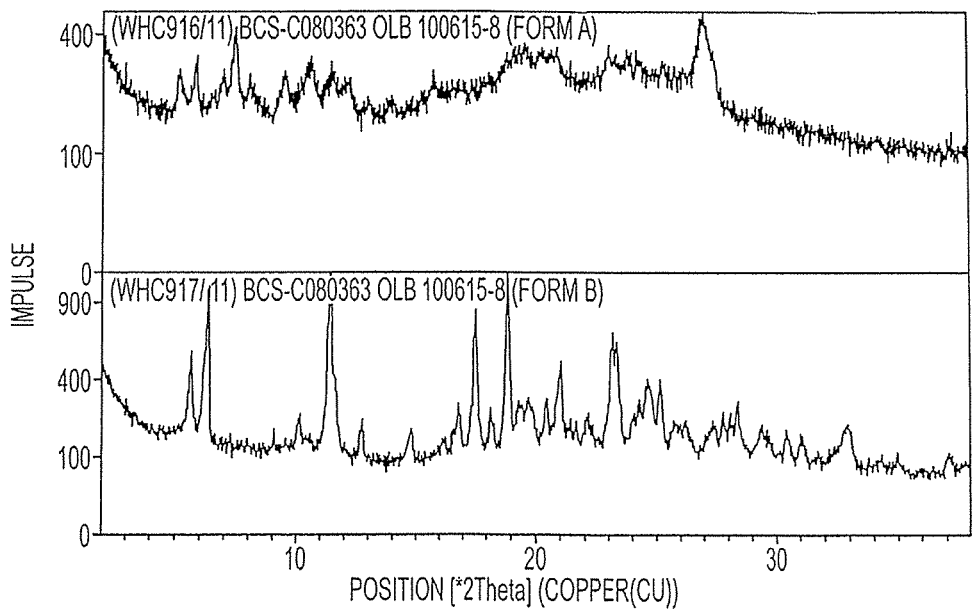
Figure 3:
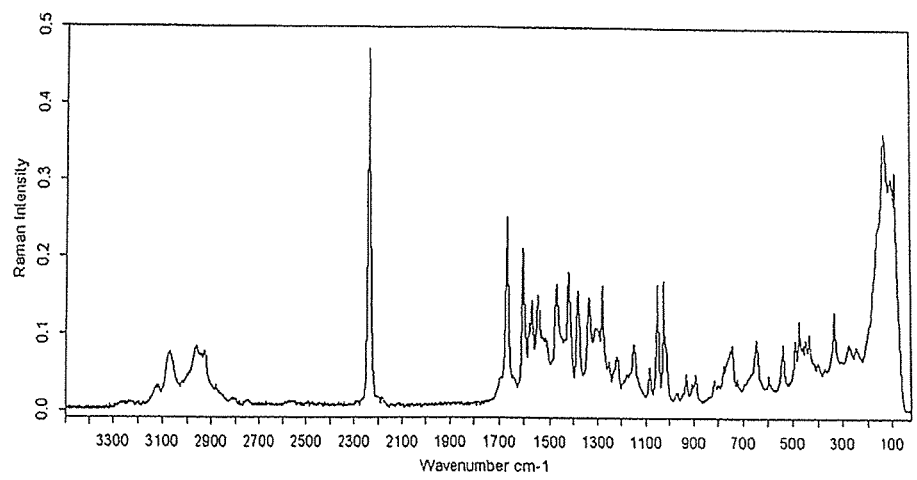
Figure 5:
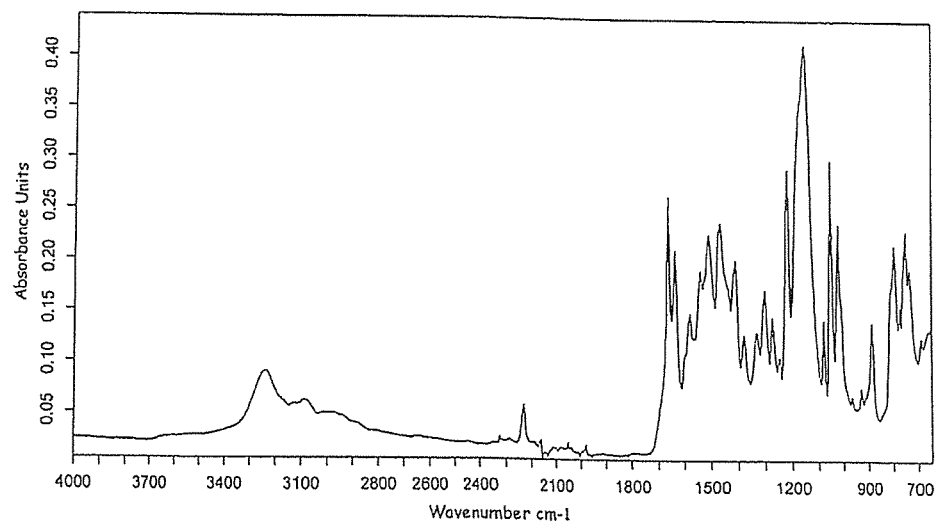

The compound of the formula (I-1) is known from WO2010/069502. To date, only one crystal form of the compound 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide of the formula (I-1) was known, which is referred to hereinafter as polymorph A. Polymorph A has a characteristic x-ray powder diffractogram, Raman spectrum and IR spectrum (Tab. 1-2, FIGS. 2, 3, 5). This crystal polymorph is thermodynamically metastable and is obtained in the form of block-like crystals.

Therefore, the process according to the invention achieved the object of providing the novel crystal polymorph B, which, due to its physicochemical properties, is easy to handle and enables the production of a stable formulation.

The invention therefore likewise provides the crystal polymorph B, which is characterized in that it has an x-ray powder diffractogram with the reflections (2 theta) specified in Table 1. The x-ray powder diffractogram of the crystal polymorph B is also reproduced in FIG. 1. The most intense signals (2 theta) of the x-ray powder diffractogram of the crystal polymorph B are accordingly at 5.7°, 6.4°, 11.4°, 17.6°, 18.9°, 21.1°, 23.2°, 23.4°, 23.5° and 25.2° (in each case±0.2°)

All x-ray powder diffractometry data of the polymorph B were obtained with the following acquisition parameters:
Diffractometer type: PANalytic X'Pert PRO
Anode material: Cu
Wavelength: 1.54060
Scan mode: Transmission
Scan type: 2theta:omega
2theta range: ±0.2°

The known crystal polymorph A of the compound of the formula (I) is characterized in that it has an x-ray powder diffractogram with the reflections (2 theta) specified in Table 1 below. The x-ray powder diffractogram of the crystal polymorph A is also reproduced in FIG. 2.

All x-ray powder diffractometry data of the polymorph A were likewise obtained with the following acquisition parameters:
Diffractometer type: PANalytic X'Pert PRO
Anode material: Cu
Wavelength: 1.54060
Scan mode: Transmission
Scan type: 2theta: omega
2theta range: ±0.2°

Figure 4:
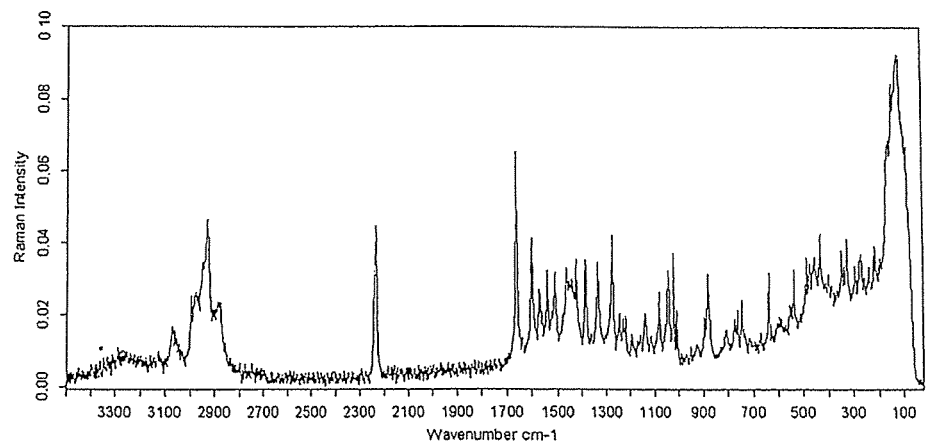
Figure 6:
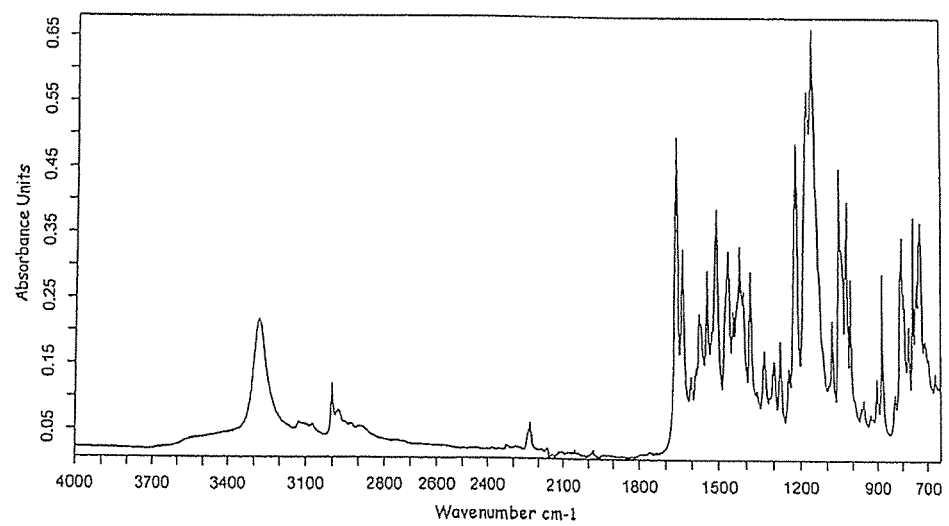
Figure 7:
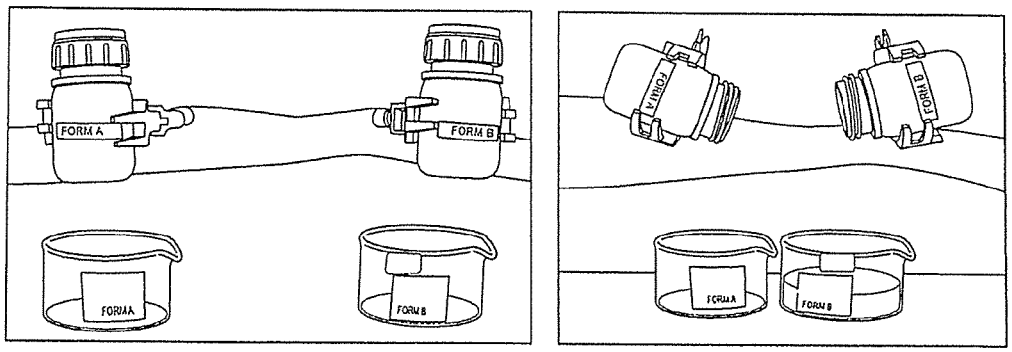
Figure 8:
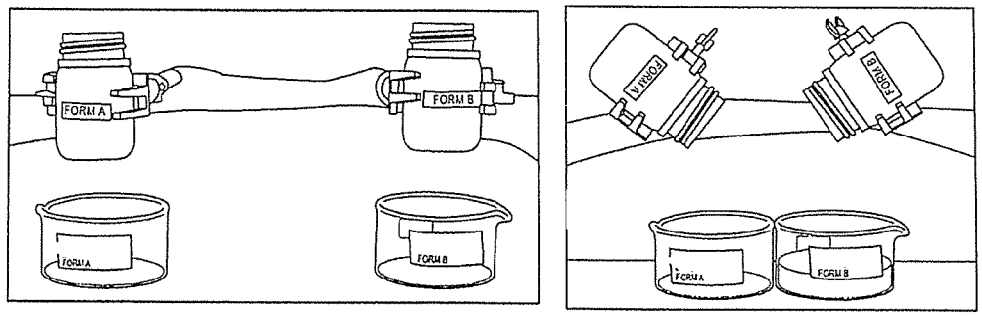
Figure 9:
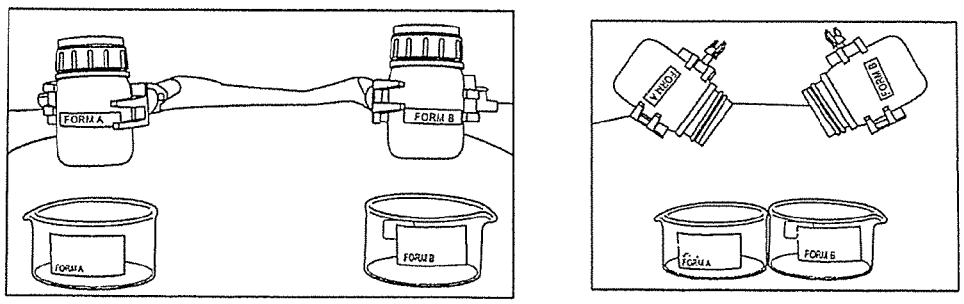
Figure 10:
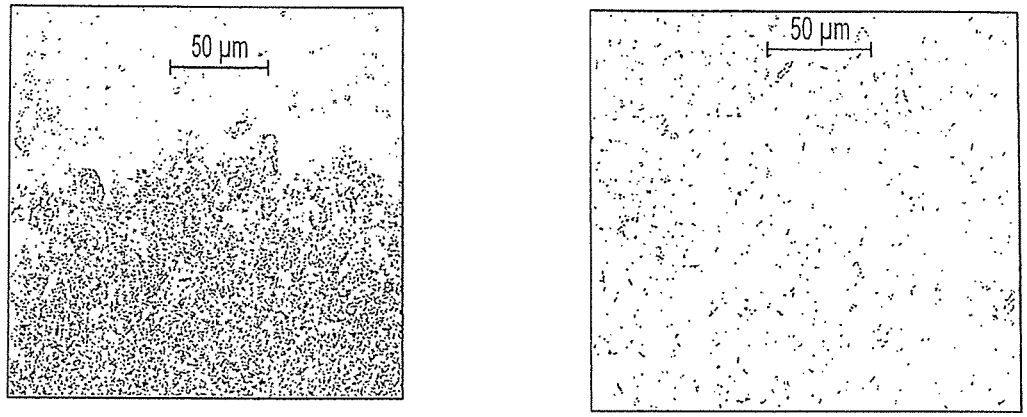
Figure 11:
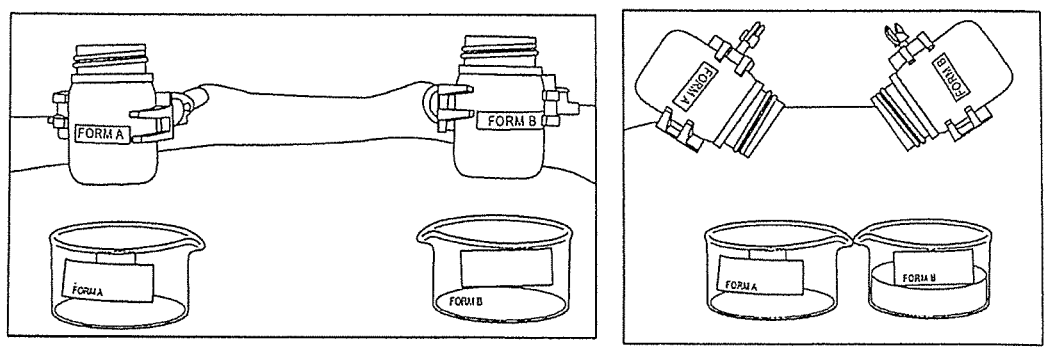
Figure 12:
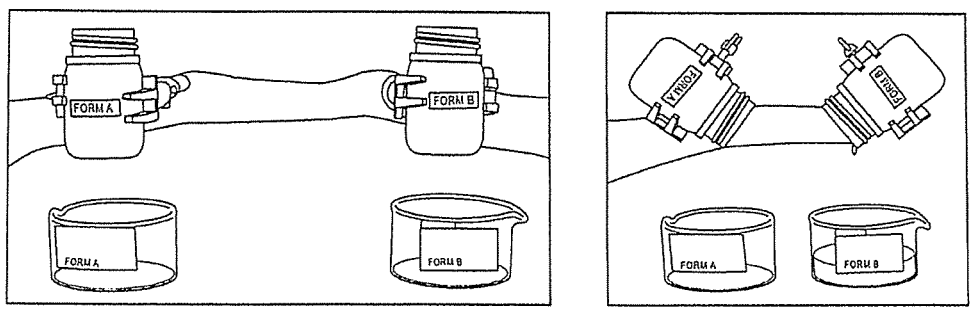
Figure 13:
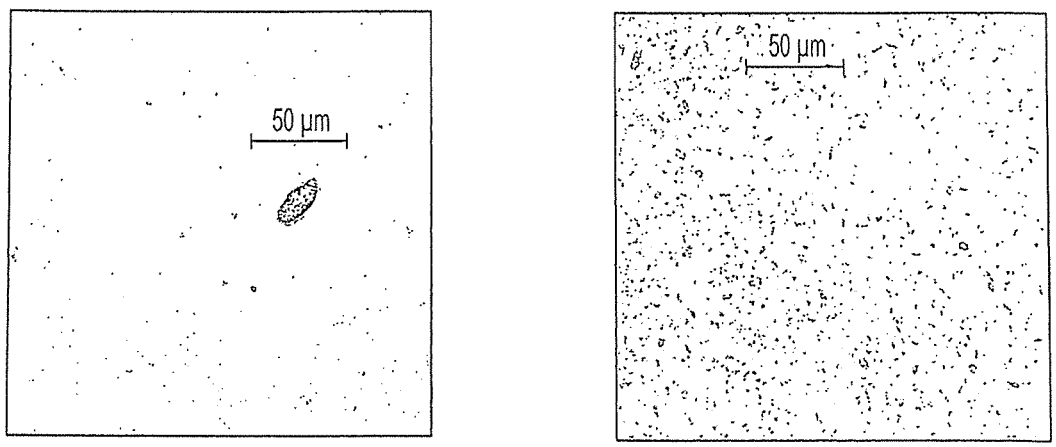
Figure 14:
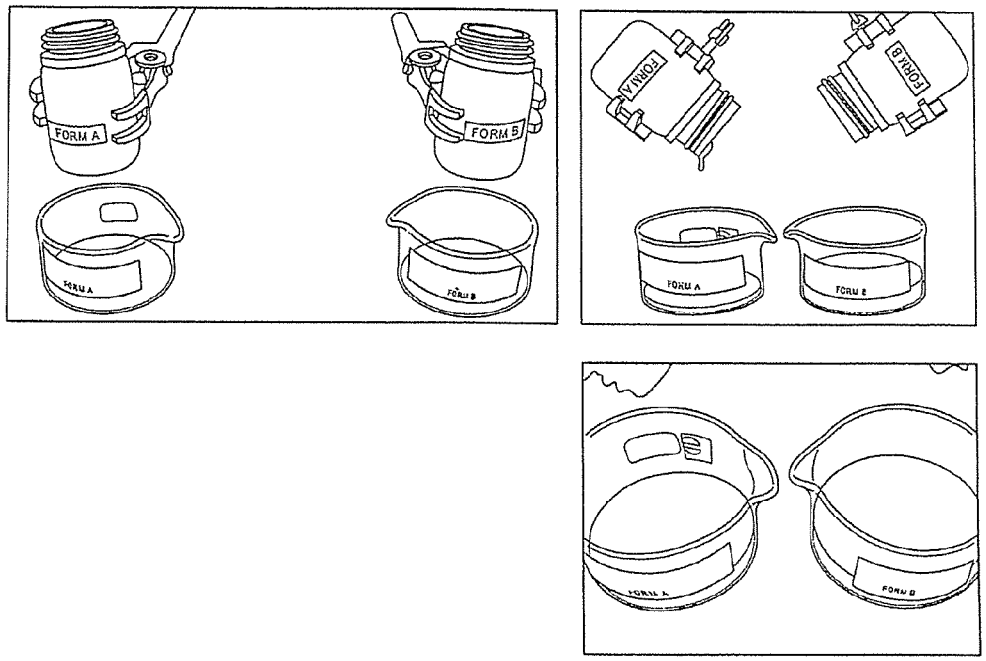
Figure 15:
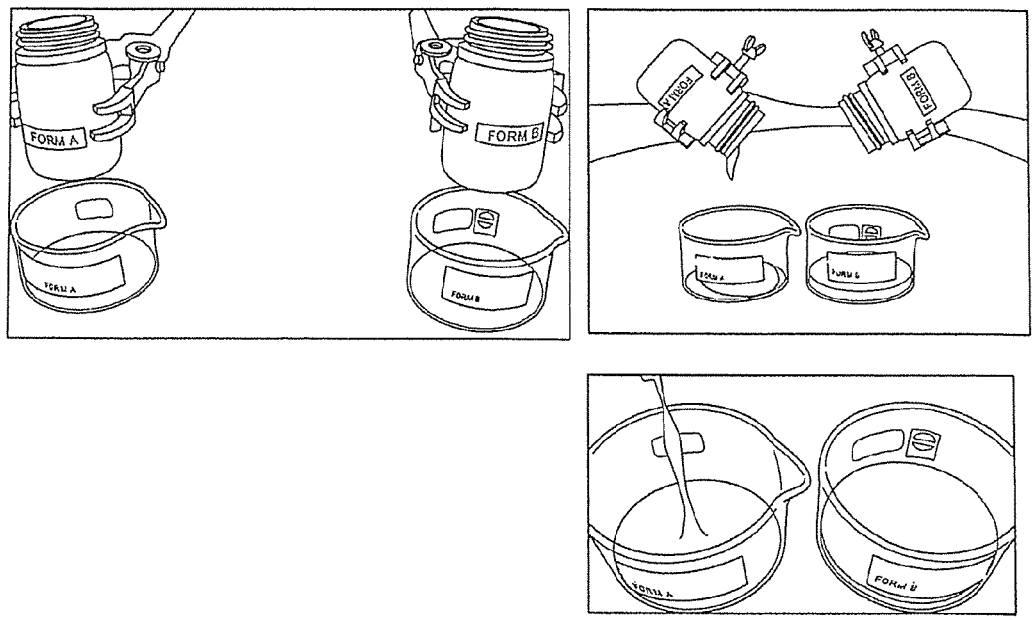

The inventive crystal polymorph B of the compound of the formula (I-1) can also be characterized by IR and Raman spectroscopy. The Raman spectra and IR Spectra of the inventive crystal polymorph B are given in FIGS. 4 and 6, respectively.

The IR and Raman spectra contain the following bands of crystal polymorphs A and B, which are listed in Table 2.

The process according to the invention by which the novel crystal polymorph B of the compound of the formula (I-1) is obtained is described in detail hereinafter:

Step 1.

Pyrazolecarboxylic esters of the formula (IV) can be prepared as follows:

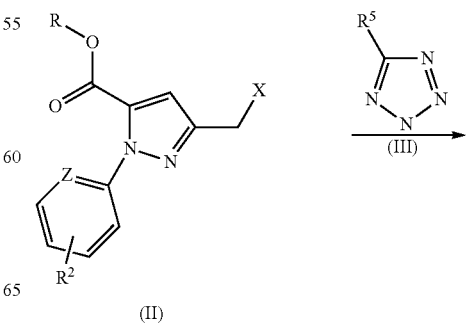

(II)  (III)

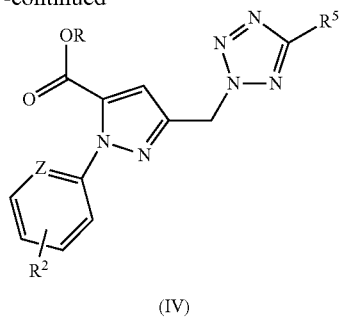

(IV)

where R, $R^2$, X, Z, $R^5$ are each as defined above.

Tetrazoles of the formula (III) are known, and some are even commercially available, or they can be obtained by known processes (cf., for example, WO2004/020445; William P. Norris, *J. Org. Chem.*, 1962, 27 (9), 3248-3251; Henry C. Brown, Robert J. Kassal, *J. Org. Chem.*, 1967, 32 (6), 1871-1873; Dennis P. Curran, Sabine Hadida, Sun-Young Kim, *Tetrahedron*, 1999, 55 (29), 8997-9006; L. D. Hansen, E. J. Baca, P. Scheiner, *Journal of Heterocyclic Chemistry*, 1970, 7, 991-996), JACS V.27, p. 3248

The alkylation of alkyltetrazoles with, for example, MeI leads typically to a mixture of 1- and 2-substituted alkyltetrazoles, the composition depending strongly on the alkylating reagent and on the substituents on the pyrazole ring. It is considered to be surprising that the alkylation of, for example, perfluoroalkyltetrazoles of the formula (III) with pyrazoles of the formula (II) takes place with high yield and high selectivity in the 2 position of the tetrazole ring, forming the 1 isomer only in amounts of 5-10%.

5-Trifluoromethyltetrazole ($R^5$=$CF_3$ in formula (III)) is a very strong organic acid with pKa 1.14, which is only slightly weaker than trifluoroacetic acid. In contrast, the trifluoromethyltetrazolyl anion is a very weak nucleophile or base. Consequently, for the alkylation of $CF_3$-tetrazoles, usually highly reactive and expensive alkyl iodides or highly reactive benzyl chlorides (see W. Finnegan et al. Journal of Organic Chemistry (1965), 30(2), 567-75) are used. The alkylation of tetrazoles with halomethylpyrazolecarboxylic acid derivatives of the formula (II) is not known, and the course of the reaction with perfluoroalkyltetrazoles of the formula (III) was not foreseeable.

It is therefore considered to be surprising that the alkylation of perfluoroalkyltetrazoles of the formula (III) with pyrazoles of the formula (II) takes place with high yield and high selectivity in the 2 position of the tetrazole ring, forming the 1 isomer only in amounts of 5-10%. It is also surprising that, during the reaction between perfluoroalkyltetrazoles of the formula (III) with, for example, chloromethylpyrazoles of the formula (II), no alkylation of the pyridine ring takes place.

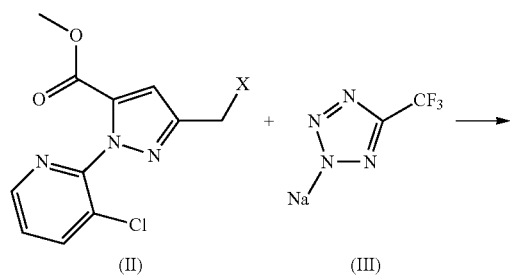

(II)      (III)

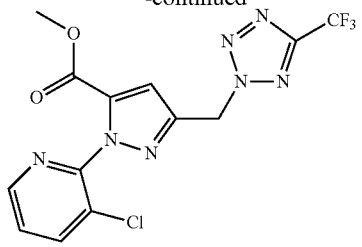

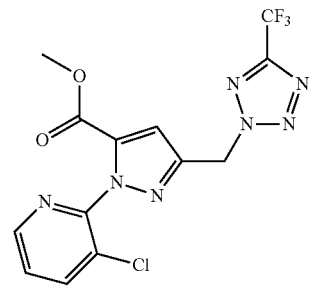

For the alkylation of, for example, $CF_3$-tetrazoles of the formula (III) with chloromethylpyrazoles of the formula (II) (X=Cl), it is necessary to accelerate the reaction by use of catalyst. The catalysts used are organic and inorganic bromides such as KBr, CsBr or preferably iodides such as KI, NaI, CsI, $Me_4NI$, $Bu_4NI$.

Surprisingly, as a result of the catalysts being present, the alkylation can be performed with weakly reactive chloromethylpyrazoles of the formula (II), and so there is no need to use the more expensive iodides as described in JACS V.27, p. 3248. At the same time, the regioselectivity of the reaction is not adversely affected. The catalysts are used in amounts between 0.1 to 1 mol, preferably 0.1-0.5 mol, based on pyrazole of the formula (II).

The process step according to the invention is performed preferably within a temperature range from 40° C. to +120° C., more preferably at temperatures of 40° C. to +80° C.

Process step (1) according to the invention is generally performed under standard pressure. Alternatively, however, it is also possible to work under reduced pressure or under pressure.

The reaction time is not critical and can, depending on the batch size, on the substituent $R^5$ in the pyrazole ring and on the temperature, be selected within a range between one and several hours.

In the performance of the process step according to the invention, for 1 mol of the pyrazole of the formula (II), 0.8 mol to 1.4 mol, preferably 0.9 mol to 1.2 mol, more preferably 1.1 mol of the tetrazole of the formula (III) is used.

The reaction is always performed in the presence of a base. Suitable bases are, for example, sodium hydroxide, potassium carbonate, sodium carbonate, caesium carbonate, sodium methoxide, triethylamine or sodium hydride. Preference is given to using the tetrazole of the formula (III) in the form of the sodium salt.

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, carbon tetrachloride, dichloroethane or trichloroethane; ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide; sulphoxides such as dimethyl sulphoxide, or sulphones such as sulpholane, alcohols such as methanol, ethanol, isopropanol. Particular preference is given to using acetone, acetonitrile, toluene, methyl tert-butyl ether, THF. The two regioisomers can be separated by chromatography, crystallization, or the mixture can be converted further without purification.

The products formed can be used without prior workup in the subsequent step, (2), in which hydrolysis takes place.

Pyrazolecarboxylic ester derivatives of the formula (II) are known or can be obtained by known processes (cf., for example, WO2007/144100).

Step 2

The compounds of the formula (IV) formed in step 1 are converted to pyrazolecarboxylic acids of the formula (V):

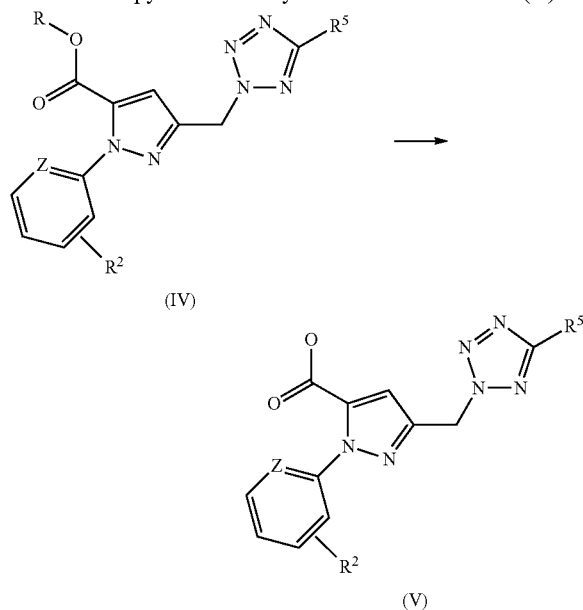

The hydrolysis is generally performed under acidic or basic conditions.

For acidic hydrolysis preference is given to mineral acids, for example $H_2SO_4$, HCl, $HSO_3Cl$, HF, HBr, HI, $H_3PO_4$, or organic acids, for example $CF_3COOH$, p-toluenesulphonic acid, methanesulphonic acid, trifluoromethanesulphonic acid. The reaction can be accelerated by the addition of catalysts, for example $FeCl_3$, $AlCl_3$, $BF_3$, $SbCl_3$, $NaH_2PO_4$. The reaction can likewise be performed without addition of acid, merely in water.

Basic hydrolysis is effected in the presence of inorganic bases such as alkali metal hydroxides, for example lithium, sodium or potassium hydroxide, alkali metal carbonates, for example $Na_2CO_3$, $K_2CO_3$, and acetates, for example NaOAc, KOAc, LiOAc, and alkoxides, for example NaOMe, NaOEt, NaOt-Bu, KOt-Bu. of organic bases such as trialkylamines, alkylpyridines, phosphazenes and 1,8-diazabicyclo[5.4.0]undecene (DBU). Preference is given to the inorganic bases such as NaOH, KOH, $Na_2CO_3$, $K_2CO_3$.

Process step (2) according to the invention is performed preferably within a temperature range from 20° C. to +150° C., more preferably at temperatures of 30° C. to +110° C., more preferably at 30-80° C.

Process step (2) according to the invention is generally performed under standard pressure. Alternatively, however, it is also possible to work under reduced pressure or under elevated pressure (for example reaction in an autoclave with aqueous HCl).

The reaction time can, depending on the batch size and the temperature, be selected within a range between 1 hour and several hours.

Reaction step 2 can be performed in substance or in a solvent. Preference is given to performing the reaction in a solvent. Suitable solvents are, for example, selected from the group consisting of water, alcohols such as methanol, ethanol, isopropanol or butanol, aliphatic and aromatic hydrocarbons, for example n-hexane, benzene or toluene, which may be substituted by fluorine and chlorine atoms, such as methylene chloride, dichloroethane, chlorobenzene or dichlorobenzene; ethers, for example diethyl ether, diphenyl ether, methyl tert-butyl ether, isopropyl ethyl ether, dioxane, diglyme, dimethylglycol, dimethoxyethane (DME) or THF; nitriles such as methyl nitrile, butyl nitrile or phenyl nitrile; amides such as dimethylformamide (DMF) or N-methylpyrrolidone (NMP) or mixtures of such solvents, and water, acetonitrile, dichloromethane and alcohols (ethanol) are particularly suitable.

Step 3.

The compounds of the formula (V) formed in step 2 are converted to anthranilamide derivatives of the formula (I).

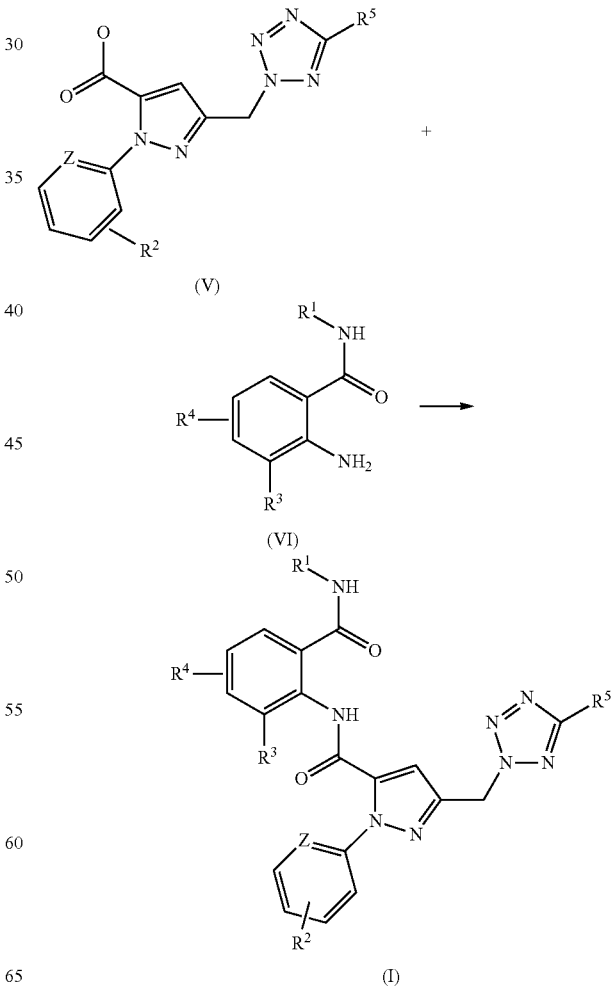

The compounds of the formula (VI) where R1 is preferably (C1-C6) alkyl are used.

Stage 3 is performed in the presence of a condensing agent. All agents customary for such coupling reactions are suitable for this purpose. Examples include acid halide formers such as phosgene, phosphorus tribromide, phosphorus trichloride, phosphorus pentachloride, phosphorus oxychloride or thionyl chloride; anhydride formers such as ethyl chloroformate, methyl chloroformate, isopropyl chloroformate, isobutyl chloroformate or methanesulphonyl chloride; carbodiimides such as N,N'-dicyclohexylcarbodiimide (DCC), or other customary condensing agents such as phosphorus pentoxide, polyphosphoric acid, 1,1'-carbonyldiimidazole, 2-ethoxy-N-ethoxycarbonyl-1,2-dihydroquinoline (EEDQ), triphenylphosphine/carbon tetrachloride, bromotripyrrolidinophosphonium hexafluorophosphate, bis(2-oxo-3-oxazolidinyl)phosphine chloride or benzotriazol-1-yloxytris(dimethylamino)phosphonium hexafluorophosphate. Polymer-supported reagents, for example polymer-supported cyclohexylcarbodiimide, can likewise be used.

Preference is given to phosgene, mesyl chloride and thionyl chloride.

Process step 3 can optionally be performed in the presence of an inert organic diluent customary for such reactions. These preferably include aliphatic, alicyclic or aromatic hydrocarbons, for example petroleum ether, hexane, heptane, cyclohexane, methylcyclohexane, benzene, toluene, xylene or decalin; halogenated hydrocarbons, for example chlorobenzene, dichlorobenzene, dichloromethane, chloroform, carbon tetrachloride, dichloroethane or trichloroethane; ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones such as acetone, butanone, methyl isobutyl ketone or cyclohexanone; nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide, or mixtures thereof.

Process step 3 is generally performed in the presence of a base.

Suitable bases are alkali metal hydroxides, for example lithium, sodium or potassium hydroxide, alkali metal carbonates, for example Na2CO3, K2CO3, and acetates, for example NaOAc, KOAc, LiOAc, and alkoxides, for example NaOMe, NaOEt, NaOt-Bu, KOt-Bu. of organic bases such as trialkylamines, alkylpyridines, phosphazenes and 1,8-diazabicyclo[5.4.0]undecene (DBU). Preference is given to the organic bases such as pyridines, alkylpyridines such as 2,6-dimethylpyridine, 2-methyl-5-ethylpyridine, 2,3-dimethylpyridine.

Process step (2) according to the invention is performed preferably within a temperature range from 20° C. to +100° C., more preferably at temperatures of 30° C. to +80° C., more preferably at 30-60° C.

Process step (2) according to the invention is generally performed under standard pressure. Alternatively, however, it is also possible to work under reduced pressure or under elevated pressure in an autoclave.

The reaction time can, depending on the batch size and the temperature, be selected within a range between 1 hour and several hours.

Process step (3) can optionally be performed in the presence of a catalyst. Examples include 4-dimethylaminopyridine, 1-hydroxybenzotriazole.

Compounds of the formula (VI) are known or can be prepared by general synthesis methods (cf., for example, Baker et al. J. Org. Chem. 1952, 149-153; G. Reissenweber et al., Angew. Chem 1981, 93, 914-915, P. J. Montoya-Pelaez, J. Org. Chem. 2006, 71, 5921-5929; F. E. Sheibley, J. Org. Chem. 1938, 3, 414-423, WO 2006023783).

If, for example, 2-amino-N-tert-butyl-5-chloro-3-methylbenzamide and 1-(3-chloropyridin-2-yl)-3-{[5-(trifluoromethyl)-2H-tetrazol-2-yl]ethyl}-1H-pyrazole-5-carboxylic acid are used as starting materials, the course of the process can be illustrated by the formula scheme below.

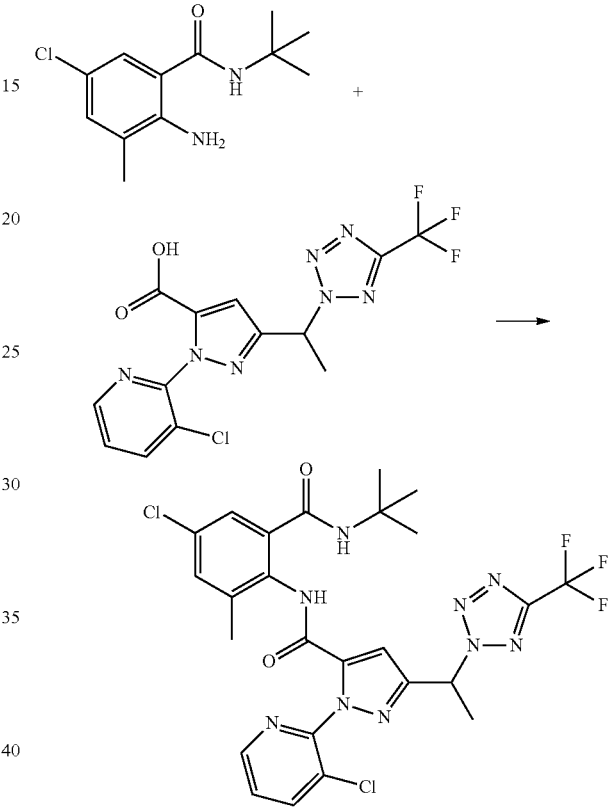

Preparation Examples

The preparation examples which follow illustrate the invention without restricting it.

Example 1

Isomer mixture of methyl 5-(3-chloropyridin-2-yl)-3-{[5-(trifluoromethyl)-2H-tetrazol-2-yl]methyl}cyclopenta-1,3-diene-1-carboxylate (main isomer) and methyl 5-(3-chloropyridin-2-yl)-3-{[5-(trifluoromethyl)-1H-tetrazol-2-yl]methyl}cyclopenta-1,3-diene-1-carboxylate (secondary component)

2.86 g (0.01 mol) of methyl 3-(chloromethyl)-1-(3-chloropyridin-2-yl)-1H-pyrazole-5-carboxylate and 1.6 g of sodium 5-(trifluoromethyl)tetrazol-2-ide and 0.15 g of KI in 50 ml of acetone were heated at 56° C. for 9 h. The salts were filtered off and acetone was removed under reduced pressure. This gave 4.59 g of the product as a 9:1 mixture of the two isomers.

Analytical Characterization
Main Isomer
$^1$H NMR (CD$_3$CN) δ: 8.52 (1H, d); 7.95 (1H, d), 7.45 (1H, dd); 7.10 (1H, s); 6.05 (2H, s); 3.75 (3H, s) ppm.
$^{19}$F NMR −64.05 ppm.
Secondary Component
$^{19}$F NMR −61.46 ppm.
$^1$H NMR (CD$_3$CN) δ: 8.50 (1H, d); 7.90 (1H, d), 7.45 (1H, dd); 6.95 (1H, s); 5.80 (2H, s); 3.70 (3H, s) ppm.

Example 2

1-(3-Chloropyridin-2-yl)-3-{[5-(trifluoromethyl)-2H-tetrazol-2-yl]methyl}-1H-pyrazole-5-carboxylic acid (main isomer) and 1-(3-chloropyridin-2-yl)-3-[5-(trifluoromethyl)-1H-tetrazol-1-yl]-1H-pyrazole-5-carboxylic acid (secondary component)

4.59 g of the mixture from Example 1 were dissolved in 40 ml of methanol, and 2 g of NaOH were added as a 10% solution in water. The mixture was stirred at RT for 3 h.

10% HCl was added in order to adjust the pH of the solution to 3, and the product was extracted with methyl tert-butyl ether. After the removal of the solvent, the residue (4 g) is converted further without purification.

Analytical characterization main isomer 90%
$^1$H NMR (CD$_3$CN) δ: 13.5 (b.s); 8.52 (1H, d); 8.2 (1H, d); 7.6 (1H, dd); 7.2 (1H, s); 6.25 (2H, s) ppm.
$^{19}$F NMR 64.25-ppm.

Example 3

Isomer mixture of 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (main isomer) and 1-(3-chloropyridin-2-yl)-N-[4-cyano-2-methyl-6-(methylcarbamoyl)phenyl]-3-[5-(trifluoromethyl)-1H-tetrazol-1-yl]-1H-pyrazole-5-carboxamide (secondary component) in a ratio of 94:6.

10 g of 1-(3-chloropyridin-2-yl)-3-{[5-(trifluoromethyl)-2H-tetrazol-2-yl]methyl}-1H-pyrazole-5-carboxylic acid and 1-(3-chloropyridin-2-yl)-3-[5-(trifluoromethyl)-1H-tetrazol-1-yl]-1H-pyrazole-5-carboxylic acid as a 90:10 mixture were initially charged in 40 ml of dimethylacetamide. 4.75 g of 2-amino-5-cyano-N,3-dimethylbenzamide, 7.2 g of 2,6-dimethylpyridine and 3.9 g of mesyl chloride were added and the mixture was stirred at 50° C. for 4 h. The mixture was cooled to 20° C. and 100 ml of water were added. After approx. 1 h, the precipitate was filtered off, washed with water and dried. This gives 12.1 g of the product (93% yield) with an isomer ratio of 94:6 and a purity of 95-96%.
Analytical Characterization
Main Isomer 94%

| H/C | δH/ppm | Mult. | rel. no. of H | δC/ppm | Mult. | rel. no. of C |
|---|---|---|---|---|---|---|
| 1 | — | — | — | 118.7 | Q | 1 |
| 2 | — | — | — | 156.1 | Q | 1 |
| 3 | 6.34 | S | 2 | 51.3 | T | 1 |
| 4 | — | — | — | 145.6 | S | 1 |
| 5 | 7.40 | S | 1 | 108.5 | D | 1 |
| 6 | — | — | — | 138.8 | S | 1 |
| 7 | — | — | — | 156.3 | S | 1 |
| 8 | 10.55 | S | 1 | — | — | — |
| 9 | — | — | — | 137.6 | S | 1 |
| 10 | — | — | — | 138.7 | S | 1 |
| 11 | — | — | — | 166.2 | S | 1 |
| 12 | 8.38 | Q | 1 | — | — | — |
| 13 | 2.66 | D | 3 | 26.3 | Q | 1 |
| 14 | 7.75 | D | 1 | 129.7 | D | 1 |
| 15 | — | — | — | 109.4 | S | 1 |
| 16 | — | — | — | 118.3 | S | 1 |
| 17 | 7.87 | D | 1 | 135.2 | D | 1 |
| 18 | — | — | — | 138.0 | S | 1 |
| 19 | 2.20 | S | 3 | 18.0 | Q | 1 |
| 20 | — | — | — | 149.1 | S | 1 |
| 21 | — | — | — | 128.0 | S | 1 |
| 22 | 8.16 | DD | 1 | 139.4 | D | 1 |
| 23 | 7.60 | DD | 1 | 126.7 | D | 1 |
| 24 | 8.48 | DD | 1 | 147.3 | D | 1 |

Secondary Component

| H/C | δH/ppm | Mult. | rel. no. of H | δC/ppm | Mult. | rel. no. of C |
|---|---|---|---|---|---|---|
| 1 | — | — | — | 118.1 | Q | 1 |
| 2 | — | — | — | 145.9 | Q | 1 |
| 3 | 6.11 | S | 2 | 47.0 | T | 1 |
| 4 | — | — | — | 145.9 | S | 1 |
| 5 | 7.35 | S | 1 | 107.7 | D | 1 |
| 6 | — | — | — | 138.8 | S | 1 |
| 7 | — | — | — | 156.2 | S | 1 |
| 8 | 10.54 | S | 1 | — | — | — |
| 9 | — | — | — | 137.6 | S | 1 |
| 10 | — | — | — | 135.2 | S | 1 |
| 11 | — | — | — | 166.2 | S | 1 |
| 12 | 8.37 | Q | 1 | — | — | — |
| 13 | 2.66 | D | 3 | 26.3 | Q | 1 |
| 14 | 7.75 | D | 1 | 129.7 | D | 1 |
| 15 | — | — | — | 109.3 | S | 1 |
| 16 | — | — | — | 118.3 | S | 1 |
| 17 | 7.87 | D | 1 | 135.4 | D | 1 |
| 18 | — | — | — | 138.0 | S | 1 |
| 19 | 2.19 | S | 3 | 17.9 | Q | 1 |
| 20 | — | — | — | 149.1 | S | 1 |
| 21 | — | — | — | 128.1 | S | 1 |
| 22 | 8.14 | DD | 1 | 139.4 | D | 1 |
| 23 | 7.58 | DD | 1 | 126.7 | D | 1 |
| 24 | 8.47 | DD | 1 | 147.2 | D | 1 |

Example 4

1-(3-Chloropyridin-2-yl)-3-{[5-(trifluoromethyl)-2H-tetrazol-2-yl]methyl}-1H-pyrazole-5-carboxylic acid (main isomer) and 1-(3-chloropyridin-2-yl)-3-[5-(trifluoromethyl)-1H-tetrazol-1-yl]-1H-pyrazole-5-carboxylic acid (secondary component)

105 g (0.36 mol) of methyl 3-(chloromethyl)-1-(3-chloropyridin-2-yl)-1H-pyrazole-5-carboxylate with a purity of 98%, 204 g (0.384 mol) of sodium 5-(trifluoromethyl)tetrazol-2-ide (30% solution in acetone) and 24 g (0.144 mol) of KI in 680 ml of acetone were heated at 56° C. for 10 h. The salts were filtered off and acetone was removed under reduced pressure. The product (oil) was taken up in 300 ml of toluene and the solution was washed with 100 ml of water. The toluenic solution was then stirred with 170 g of 10% solution of NaOH at 40° C. for 6 h. The organic phase was removed and the aqueous phase was adjusted gradually to pH 3 with 10% HCl. The precipitated product was filtered off, washed with water and dried. This gave 118 g (85% yield) of the product with a w.w. % purity of 97.3%. Ratio of regioisomers 94:6.

The present invention further relates to formulations and use forms prepared therefrom as crop protection compositions and/or pesticides, for example drench, drip and spray liquors. In some cases, the use forms comprise further crop protection compositions and/or pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulphate or diammonium hydrogenphosphate and/or retention promoters, for example dioctyl sulphosuccinate or hydroxypropyl guar polymers and/or humectants, for example glycerol and/or fertilizers, for example ammonium-, potassium- or phosphorus-containing fertilizers.

Customary formulations relating to the present invention are, for example, suspension concentrates (SC, SE, FS, OD), water-dispersible granules (WG) and granules (GR); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations optionally comprise, in addition to one or more inventive active ingredients, further active agrochemical ingredients.

These are preferably formulations or use forms which comprise auxiliaries, for example extenders, solvents, spontaneity promoters, carriers, emulsifiers, dispersants, frost protectants, biocides, thickeners and/or further auxiliaries, for example adjuvants. An adjuvant in this context is a component which enhances the biological effect of the formulation, without the component itself having a biological effect. Examples of adjuvants are agents which promote retention, spreading, attachment to the leaf surface or penetration.

These formulations are produced in a known manner, for example by mixing the active ingredients with auxiliaries, for example extenders, solvents and/or solid carriers and/or further auxiliaries, for example surfactants. The formulations are produced either in suitable plants or else before or during application.

The auxiliaries used may be substances suitable for imparting special properties, such as certain physical, technical and/or biological properties, to the formulation of the active ingredient, or to the use forms prepared from these formulations (for example ready-to-use crop protection compositions such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to use, for example, organic solvents as auxiliary solvents. Useful liquid solvents are essentially: aromatics such as xylene, toluene or alkylnaphthalenes, chlorinated aromatics and chlorinated aliphatic hydrocarbons such as chlorobenzenes, chloroethylenes or dichloromethane, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

In principle it is possible to use all suitable carriers. Useful carriers include especially: for example ammonium salts and ground natural minerals such as kaolins, clays, talc, chalk, quartz, attapulgite, montmorillonite or diatomaceous earth, and ground synthetic materials such as finely divided silica, alumina and natural and synthetic silicates, resins, waxes and/or solid fertilizers. Mixtures of such carriers can likewise be used. Useful carriers for granules include: for example crushed and fractionated natural rocks such as calcite, marble, pumice, sepiolite, dolomite, and synthetic granules of inorganic and organic meals, and also granules of organic material such as sawdust, paper, coconut shells, maize cobs and tobacco stalks.

Examples of emulsifiers and/or foam formers, dispersants or wetting agents with ionic or nonionic properties, or mixtures of these surfactants, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkylsulphates, arylsulphonates, protein hydrolysates, lignosulphite waste liquors and methylcellulose. The presence of a surfactant is advantageous when one of the active ingredients and/or one of the inert carriers is insoluble in water and when application is effected in water. Further auxiliaries which may be present in the formulations and the use forms derived therefrom include dyes such as inorganic pigments, for example iron oxide, titanium oxide and Prussian Blue, and organic dyes such as alizarin dyes, azo dyes and metal phthalocyanine dyes, nutrients and trace nutrients such as salts of iron, manganese, boron, copper, cobalt, molybdenum and zinc.

Additional components may be stabilizers, such as cold stabilizers, preservatives, antioxidants, light stabilizers, or other agents which improve chemical and/or physical stability. Foam formers or antifoams may also be present.

The formulations and the use forms derived therefrom may also comprise, as additional auxiliaries, tackifiers such as carboxymethylcellulose, natural and synthetic polymers in the form of powders, granules or latices, such as gum arabic, polyvinyl alcohol and polyvinyl acetate, and also natural phospholipids such as cephalins and lecithins, and synthetic phospholipids. Further auxiliaries may be mineral and vegetable oils.

If appropriate, the formulations and the use forms derived therefrom may also comprise further auxiliaries. Examples of such additives include fragrances, protective colloids, binders, adhesives, thickeners, thixotropic agents, penetrants, retention promoters, stabilizers, sequestrants, complexing agents, humectants, spreaders. In general, the active ingredients can be combined with any solid or liquid additive commonly used for formulation purposes.

Useful retention promoters include all those substances which reduce the dynamic surface tension, for example dioctyl sulphosuccinate, or increase the viscoelasticity, for example hydroxypropylguar polymers.

Useful penetrants in the present context are all those substances which are typically used to improve the penetration of active agrochemical ingredients into plants. Penetrants are defined in this context by their ability to penetrate from the (generally aqueous) spray liquor and/or from the spray coating into the cuticle of the plant and thereby increase the mobility of active ingredients in the cuticle. The method described in the literature (Baur et al., 1997, Pesticide Science 51, 131-152) can be used to determine this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations preferably comprise between 0.00000001% and 98% by weight of active ingredient or, more preferably, between 0.01% and 95% by weight of active ingredient, more preferably between 0.5% and 90% by weight of active ingredient, based on the weight of the formulation.

The active ingredient content of the use forms (crop protection compositions) prepared from the formulations may vary within wide limits. The active ingredient concentration of the use forms may typically be between 0.00000001% and 95% by weight of active ingredient, preferably between 0.00001% and 1% by weight, based on the weight of the use form. Application is accomplished in a customary manner appropriate for the use forms.

The examples which follow illustrate the invention without restricting it. The solvent systems used in the examples which follow are particularly preferred. The inventive compound of the formula (I-1) was formulated in three different formulation recipes with three different concentrations to give water-based suspension concentrates (formulation examples 1, 2 and 3). The compound of the formula (I-1) as the active ingredient was used both in the A form and in the B form. Subsequently, the suspension concentrates produced were stored under the same conditions and, after the end of the storage, analysed with regard to their properties. It was found that, surprisingly, the suspension concentrates produced with the compound of the formula (I-1) as form B differed considerably in terms of properties from the suspension concentrates which had been produced with the compound of the formula (I-1) as form A.

Formulation Example

Example 1

To produce a suspension concentrate, the following are combined at room temperature:

| | | |
|---|---|---|
| 7.28 | % by weight | compound (I-1) in form A |
| 0.20 | % by weight | aqueous silicone oil emulsion, e.g. Silfoam SRE (from Wacker) |
| 0.20 | % by weight | citric acid |
| 0.12 | % by weight | aqueous benzoisothiazolinone solution, e.g. Proxel GXL 20% |
| 0.08 | % by weight | mixture of biocides of the isothiazolone type in aqueous solution, e.g. Preventol D7 |

-continued

| | | |
|---|---|---|
| 0.50 | % by weight | sodium alkylnaphthalenesulphonate-formaldehyde condensate, e.g. Morwet D-425 (from Akzo-Nobel) |
| 10.00 | % by weight | glycerol |
| 4.00 | % by weight | ethoxylated polymethacrylate, e.g. Atlox 4913 (from Croda) |
| 1.50 | % by weight | tristyrylphenol ethoxylate, e.g. Tanemul PS 54 (from Tanatex) |
| 56.02 | % by weight | demineralized water | and, after addition has ended, the mixture is stirred at room temperature for another 10 minutes. The resulting homogeneous suspension is subjected first to coarse grinding and then to fine grinding, such that a suspension is obtained in which 90% of the solid particles have a particle size below 6 μm. This is then made up with

| | | |
|---|---|---|
| 0.10 | % by weight | xanthan thickener, e.g. Kelzan S (from CP Kelco) |
| 20.00 | % by weight | demineralized water |

The Kelzan S is used as a 2% preliminary mixture. Subsequently, the suspension is stirred until a homogeneous suspension has formed.

Analogously to the abovementioned experimental method, a suspension concentrate comprising the compound (I-1) in the B form is prepared.

Both suspension concentrates (form A and form B) are homogeneous and mobile immediately after preparation. Portions of both suspension concentrates are dispensed and left to stand first at room temperature for 3 days and then stored at 40° C. and 54° C. for 7 or 14 days. Subsequently, the sample bottles are brought to room temperature, homogenized if appropriate by shaking gently, and compared.

Example 2

To produce a suspension concentrate, the following are combined at room temperature:

| | | |
|---|---|---|
| 8.47 | % by weight | compound (I-1) in form A |
| 0.20 | % by weight | aqueous silicone oil emulsion, e.g. Silfoam SRE |
| 0.20 | % by weight | citric acid |
| 0.12 | % by weight | aqueous benzoisothiazolinone solution, e.g. Proxel GXL 20% |
| 0.08 | % by weight | mixture of biocides of the isothiazolone type in aqueous solution, e.g. Preventol D7 |
| 0.50 | % by weight | sodium alkylnaphthalenesulphonate-formaldehyde condensate, e.g. Morwet D-425 |
| 10.00 | % by weight | 1,2-propanediol |
| 1.00 | % by weight | EO-PO block copolymer, e.g. Synperonic PE/F 127 (from Croda) |
| 4.00 | % by weight | tristyrylphenol ethoxylate sulphate, e.g. Soprophor 4D384 (from Rhodia) |
| 0.50 | % by weight | amorphous precipitated silica, e.g. Sipernat 22S (from Evonik) |
| 54.83 | % by weight | demineralized water | and, after addition has ended, the mixture is stirred at room temperature for another 10 minutes. The resulting homogeneous suspension is subjected first to coarse grinding and then to fine grinding, such that a suspension is obtained in which 90% of the solid particles have a particle size below 6 μm. This is then made up with

| | | |
|---|---|---|
| 0.10 | % by weight | xanthan thickener, e.g. Kelzan S |
| 20.00 | % by weight | demineralized water |

The Kelzan S is used as a 2% preliminary mixture. Subsequently, the suspension is stirred until a homogeneous suspension has formed.

Analogously to the abovementioned experimental method, a suspension concentrate comprising the compound (1) in the B form is prepared.

Both suspension concentrates (form A and form B) are homogeneous and mobile immediately after preparation. Portions of both suspension concentrates are dispensed and left to stand first at room temperature for 3 days and then stored at 40° C. and 54° C. for 7 or 14 days. Subsequently, the sample bottles are brought to room temperature, homogenized if appropriate by shaking gently, and compared.

Example 2 after storage at room temperature for 3 days:

After storage at room temperature for 3 days, both samples are homogeneous and mobile.

Example 3

To produce an inventive suspension concentrate, the following are combined at room temperature:

| | | |
|---|---|---|
| 4.85 | % by weight | compound (I-1) in form A |
| 0.20 | % by weight | aqueous silicone oil emulsion, e.g. Silfoam SRE |
| 0.20 | % by weight | citric acid |
| 0.12 | % by weight | aqueous benzoisothiazolinone solution, e.g. Proxel GXL 20% |
| 0.08 | % by weight | mixture of biocides of the isothiazolone type in aqueous solution, e.g. Preventol D7 |
| 1.50 | % by weight | sodium alkylnaphthalenesulphonate-formaldehyde condensate, e.g. Morwet D-425 |
| 10.00 | % by weight | 1,2-propanediol |
| 6.25 | % by weight | ethoxylated polymethacrylate, e.g. Atlox 4913 |
| 2.00 | % by weight | butyl-EO-PO block copolymer, e.g. Atlas G-5000 (from Croda) |
| 54.60 | % by weight | demineralized water | and, after addition has ended, the mixture is stirred at room temperature for another 10 minutes. The resulting homogeneous suspension is subjected first to coarse grinding and then to fine grinding, such that a suspension is obtained in which 90% of the solid particles have a particle size below 6 μm. This is then made up with

| | | |
|---|---|---|
| 0.20 | % by weight | xanthan thickener, e.g. Kelzan S |
| 20.00 | % by weight | demineralized water |

The Kelzan S is used as a 2% preliminary mixture. Subsequently, the suspension is stirred until a homogeneous suspension has formed.

Analogously to the abovementioned experimental method, a suspension concentrate comprising the compound (I-1) in the B form is prepared.

Both suspension concentrates (form A and form B) are homogeneous and mobile immediately after preparation. Portions of both suspension concentrates are dispensed and left to stand first at room temperature for 3 days and then stored at 40° C. and 54° C. for 7 or 14 days. Subsequently, the sample bottles are brought to room temperature and compared.

Example 3 after storage at room temperature for 3 days:

After storage at room temperature for 3 days, both samples are homogeneous and mobile.

Example 3 after storage at room temperature for 3 days and at 40° C. or 54° C. for 7 days:

After storage at room temperature for 3 days and at 40° C. or 54° C. for 7 days, both samples are mobile, but show slight phase separation.

TABLE 1

X-ray powder diffractometry Reflections [2 theta]

| Polymorph A | Polymorph B |
|---|---|
| 2.9 | 5.7 |
| 5.2 | 6.4 |
| 5.9 | 7.3 |
| 6.5 | 8.3 |
| 7.0 | 9.1 |
| 7.3 | 9.6 |
| 7.4 | 10.2 |
| 8.1 | 10.6 |
| 9.6 | 11.4 |
| 10.6 | 11.7 |
| 11.6 | 12.8 |
| 12.3 | 14.9 |
| 13.1 | 16.2 |
| 14.2 | 16.8 |
| 15.9 | 17.6 |
| 18.8 | 18.2 |
| 19.6 | 18.9 |
| 20.3 | 19.3 |
| 21.0 | 19.7 |
| 22.1 | 20.0 |
| 22.7 | 20.5 |
| 23.1 | 21.1 |
| 23.8 | 21.5 |
| 24.3 | 21.8 |
| 25.4 | 22.2 |
| 25.8 | 22.9 |
| 26.9 | 23.2 |
| 27.5 | 23.4 |
| 31.3 | 23.5 |
| 32.4 | 24.0 |
| 37.2 | 24.3 |
|  | 24.6 |
|  | 25.2 |
|  | 25.8 |
|  | 25.8 |
|  | 27.3 |
|  | 27.8 |
|  | 28.0 |
|  | 28.3 |
|  | 29.4 |
|  | 29.7 |
|  | 30.4 |
|  | 31.0 |
|  | 31.7 |
|  | 32.2 |
|  | 32.9 |
|  | 34.3 |
|  | 35.0 |
|  | 37.1 |

TABLE 2

IR and Raman bands

| Polymorph A IR bands [cm$^{-1}$] | Polymorph B IR bands [cm$^{-1}$] | Polymorph A Raman bands [cm$^{-1}$] | Polymorph B Raman bands [cm$^{-1}$] |
|---|---|---|---|
| 3238 | 3280 | 3117 | 3073 |
| 3087 | 3002 | 3070 | 2997 |
| 2232 | 2977 | 2962 | 2929 |
| 1662 | 2233 | 2927 | 2881 |
| 1636 | 1661 | 2235 | 2231 |

TABLE 2-continued

IR and Raman bands

| Polymorph A IR bands [cm$^{-1}$] | Polymorph B IR bands [cm$^{-1}$] | Polymorph A Raman bands [cm$^{-1}$] | Polymorph B Raman bands [cm$^{-1}$] |
|---|---|---|---|
| 1579 | 1637 | 2231 | 2236 |
| 1541 | 1602 | 1664 | 1664 |
| 1510 | 1574 | 1601 | 1602 |
| 1468 | 1543 | 1578 | 1574 |
| 1410 | 1510 | 1567 | 1543 |
| 1379 | 1466 | 1543 | 1512 |
| 1332 | 1446 | 1516 | 1464 |
| 1304 | 1421 | 1468 | 1424 |
| 1275 | 1410 | 1419 | 1386 |
| 1249 | 1385 | 1378 | 1335 |
| 1220 | 1334 | 1332 | 1275 |
| 1155 | 1298 | 1306 | 1244 |
| 1080 | 1275 | 1277 | 1229 |
| 1054 | 1244 | 1252 | 1219 |
| 1022 | 1219 | 1218 | 1141 |
| 930 | 1178 | 1147 | 1081 |
| 887 | 1155 | 1081 | 1044 |
| 797 | 1080 | 1048 | 1022 |
| 773 | 1055 | 1021 | 1008 |
| 751 | 1046 | 966 | 897 |
| 736 | 1029 | 929 | 882 |
| 690 | 1023 | 889 | 772 |
|  | 1009 | 813 | 760 |
|  | 954 | 775 | 745 |
|  | 902 | 744 | 636 |
|  | 882 | 645 | 539 |
|  | 829 | 594 | 489 |
|  | 803 | 537 | 475 |
|  | 795 | 489 | 457 |
|  | 774 | 474 | 350 |
|  | 758 | 449 | 337 |
|  | 743 | 434 | 327 |
|  | 729 | 400 | 296 |
|  | 669 | 331 | 271 |
|  |  | 274 | 218 |
|  |  | 245 | 115 |
|  |  | 129 |  |
|  |  | 100 |  |
|  |  | 84 |  |

The invention claimed is:

1. A process for preparing a compound of formula (I), or a N-oxide or a salt thereof

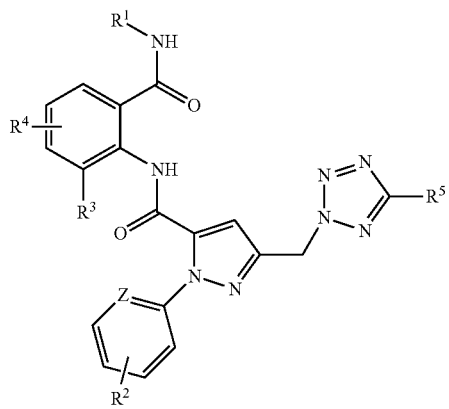

(I)

in which
R$^1$, R$^3$ are each independently C$_1$-C$_5$-alkyl,
R$^2$ is halogen
R$^4$ is hydrogen, chlorine, or cyano,
R$^5$ is (C$_1$-C$_3$)perfluoroalkyl, Z is N, said process comprising reacting an N-aryl- and N-hetaryl-substituted pyrazole of formula (II)

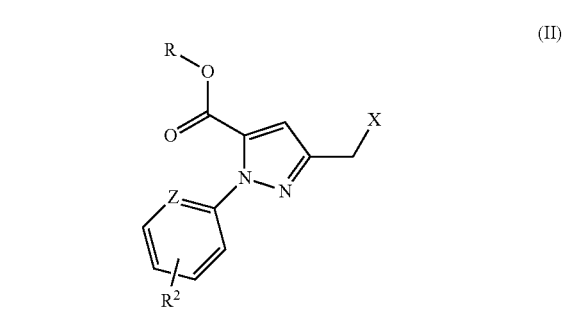

(II)

in which
R is C$_1$-C$_6$-alkyl, aryl(C$_1$-C$_6$)alkyl or aryl
and X is fluorine, chlorine, bromine, iodine, CH$_3$SO$_2$O, CF$_3$SO$_3$, or p-CH$_3$—C$_6$H$_4$SO$_3$, with a tetrazole of formula (III)

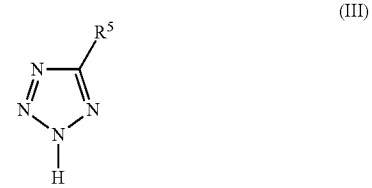

(III)

to give a pyrazolecarboxylic ester of formula (IV)

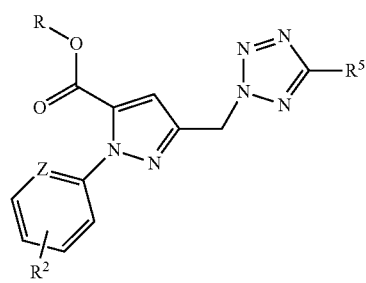

(IV)

in which
the latter are optionally hydrolysed under acidic or basic conditions without preceding isolation to a pyrazolecarboxylic acid of formula (V)

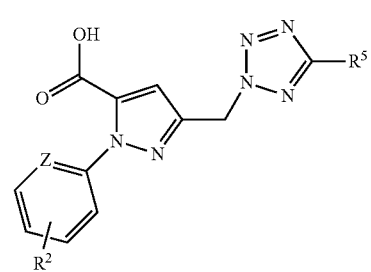

(V)

and the latter are reacted with a compound of the formula (VI)

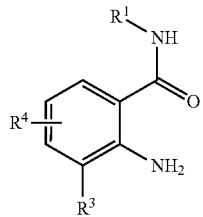

to give an anthranilamide of the formula (I)

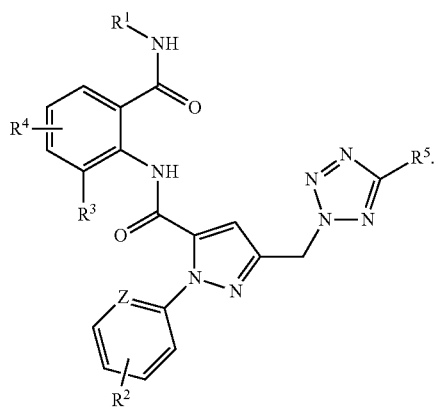

2. Process for preparing a compound according to claim 1, where
$R^1$, $R^3$ are each independently methyl, ethyl or tert-butyl,
$R^2$ is fluorine or chlorine,
$R^4$ is chlorine or cyano,
$R^5$ is $CF_3$ or $C_2F_5$,
Z is N.

3. Process for preparing a compound according to claim 1, wherein $R^5$ is $CF_3$.

4. Process for preparing a compound according to claim 1, wherein $R^2$ is chlorine, $R^3$ is methyl and $R^4$ is cyano.

5. Process according to claim 1, wherein the compound of formula (I) is a crystal polymorph of the formula (I-1)

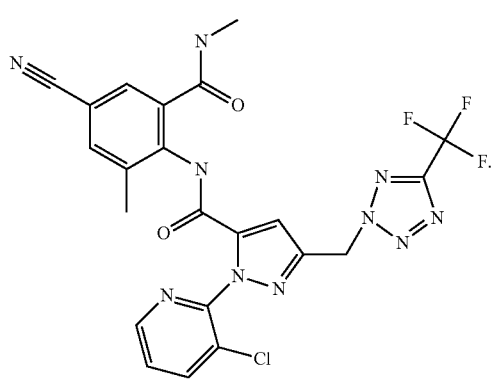

6. The process according to claim 5 wherein said crystal polymorph is crystal polymorph B which comprises an x-ray powder diffractogram using Cu Kα radiation that has at least the following reflections:

| 2theta/° |
| --- |
| 5.7 |
| 6.4 |
| 11.4 |
| 17.6 |
| 18.9 |
| 21.1 |
| 23.2 |
| 23.4 |
| 23.5 |
| 25.2. |

7. The process according to claim 6, wherein the x-ray powder diffractogram thereof of crystal polymorph B using Cu Kα radiation has at least the following further reflections:

| 2theta/° |
| --- |
| 11.7 |
| 16.8 |
| 19.7 |
| 20.5 |
| 24.3 |
| 24.6 |
| 28.3. |

8. The process according to claim 6, wherein the x-ray powder diffractogram thereof of crystal polymorph using Cu Kα radiation corresponds essentially to the spectrum reproduced in FIG. 1.

9. The process according to claim 6, wherein said crystal polymorph B of the compound of the formula (I-1) has a Raman spectrum that has at least the following bands:

| Band [cm$^{-1}$] |
| --- |
| 2929 |
| 1386 |
| 882 |
| 636. |

10. The process according to claim 6, wherein said crystal polymorph B has a Raman spectrum that corresponds essentially to the spectrum reproduced in FIG. 4.

* * * * *